(12) United States Patent
Jakimov et al.

(10) Patent No.: US 10,427,244 B2
(45) Date of Patent: Oct. 1, 2019

(54) CONTROL IN GENERATIVE PRODUCTION

(71) Applicant: MTU Aero Engines AG, Munich (DE)

(72) Inventors: Andreas Jakimov, Munich (DE); Georg Schlick, Munich (DE); Joachim Bamberg, Dachau (DE); Thomas Hess, Munich (DE)

(73) Assignee: MTU AERO ENGINES AG, Munich (DE)

( * ) Notice: Subject to any disclaimer, the term of this patent is extended or adjusted under 35 U.S.C. 154(b) by 1207 days.

(21) Appl. No.: 14/325,458

(22) Filed: Jul. 8, 2014

(65) Prior Publication Data

US 2015/0017054 A1  Jan. 15, 2015

(30) Foreign Application Priority Data

Jul. 9, 2013 (DE) .................. 10 2013 213 370

(51) Int. Cl.
| | |
|---|---|
| *B23K 26/08* | (2014.01) |
| *B23K 26/354* | (2014.01) |
| *B22F 3/105* | (2006.01) |
| *B22F 3/00* | (2006.01) |
| *B23K 15/00* | (2006.01) |
| *G01N 27/72* | (2006.01) |
| *B33Y 10/00* | (2015.01) |
| *B33Y 30/00* | (2015.01) |
| *B33Y 50/02* | (2015.01) |

(52) U.S. Cl.
CPC .............. *B23K 26/08* (2013.01); *B22F 3/003* (2013.01); *B22F 3/105* (2013.01); *B22F 3/1055* (2013.01); *B23K 15/002* (2013.01); *B23K 15/0086* (2013.01); *B23K 26/354* (2015.10); *B33Y 10/00* (2014.12); *B33Y 30/00* (2014.12); *G01N 27/72* (2013.01); *B22F 2003/1057* (2013.01); *B33Y 50/02* (2014.12); *Y02P 10/295* (2015.11)

(58) Field of Classification Search
CPC . B22F 2003/1057; B33Y 10/00; B33Y 50/02; G01N 27/90; B23K 26/08
USPC .......................................................... 419/53
See application file for complete search history.

(56) References Cited

U.S. PATENT DOCUMENTS

| | | | | |
|---|---|---|---|---|
| 5,684,616 A | * | 11/1997 | Brotz ................. | G02B 27/2285 335/216 |
| 8,034,279 B2 | | 10/2011 | Dimter et al. | |
| 2006/0244443 A1 | * | 11/2006 | Goldfine ............ | G01N 27/9046 324/236 |
| 2007/0176312 A1 | * | 8/2007 | Clark .................... | B22F 3/1055 264/40.1 |
| 2008/0241392 A1 | | 10/2008 | Dimter et al. | |
| 2009/0091318 A1 | * | 4/2009 | Lepage .............. | G01N 27/9013 324/242 |

(Continued)

FOREIGN PATENT DOCUMENTS

| | | |
|---|---|---|
| DE | 4002633 | 8/1991 |
| DE | 19835860 C1 | 4/2000 |

(Continued)

*Primary Examiner* — Weiping Zhu

(74) *Attorney, Agent, or Firm* — Abel Schillinger, LLP

(57) ABSTRACT

Disclosed is a method for generatively producing components by layer-by-layer building from a powder material by selective material bonding of powder particles by a high-energy beam. An eddy current testing is carried out concurrently with the material bonding. Also disclosed is an apparatus which is suitable for carrying out the method.

20 Claims, 2 Drawing Sheets

(56) References Cited

U.S. PATENT DOCUMENTS

2013/0233846 A1    9/2013  Jakimov et al.
2013/0343947 A1   12/2013  Satzger et al.
2014/0159266 A1*   6/2014  Bamberg .............. B22F 3/1055
                                                264/40.1

FOREIGN PATENT DOCUMENTS

| DE | 102007014683 A1 | 10/2008 |
| DE | 102010050531 A1 | 3/2012 |
| DE | 102011008774 A1 | 7/2012 |
| DE | 102011009624 A1 | 8/2012 |
| DE | 102011111818 A1 | 2/2013 |

* cited by examiner

CONTROL IN GENERATIVE PRODUCTION

CROSS-REFERENCE TO RELATED APPLICATIONS

The present application claims priority under 35 U.S.C. § 119 of German Patent Application No. 102013213370.7, filed Jul. 9, 2013, the entire disclosure of which is expressly incorporated by reference herein.

BACKGROUND OF THE INVENTION

1. Field of the Invention

The present invention relates to a method for producing a component by means of a generative production process, in which material is repeatedly applied layer by layer to a base plate or an already correspondingly generated semifinished product and is bonded with the semifinished product, wherein radiation energy which is introduced into the material by at least one beam that is moved in relation to and over the surface of the semifinished product is used for the bonding of the material with the semifinished product. The invention also relates to a corresponding apparatus for carrying out the method.

2. Discussion of Background Information

Generative production processes for producing a component, such as for example stereolithographic processes, selective laser melting, selective laser sintering, electron beam melting or laser build-up welding, are used in industry for so-called rapid tooling, rapid prototyping or else for the production of series products in rapid manufacturing. In particular, such processes may also be used for the production of turbine parts, in particular parts of aircraft engines, in the case of which such generative production processes are advantageous for example because of the material used. An example of this can be found in DE 10 2010 050 531 A1, the entire disclosure of which is incorporated by reference herein.

To achieve particularly homogeneous component properties and a low-stress structure of the component, so-called exposure strategies are described in the prior art for the relative movement of the energy beam with respect to the semifinished product. These involve changing the paths of movement of a beam, for example a laser beam, from layer to layer of the material to be deposited, in order to generate a homogeneous microstructure by means of different orientation of the structure being built up. An example of this is described in DE 10 2007 014 683 A1, the entire disclosure of which is incorporated by reference herein.

In addition, the given properties of the material and component cause variations in the process, which may lead to inhomogeneities. For example, the geometry of the component may cause the irregular removal of process gases, resulting in instability.

It would therefore be advantageous to be able to provide a further improvement of radiation-based, generative production processes by which homogeneous component properties can be achieved. At the same time, the method should be usable easily and effectively.

SUMMARY OF THE INVENTION

The present invention provides a method for generatively producing components by layer-by-layer building from a powder material by selective material bonding of powder particles by a high-energy beam. An eddy current testing is carried out concurrently with the material bonding.

In one aspect of the method, the material bonding may take place by at least one of welding and sintering.

In another aspect, the high-energy beam may be a laser beam or an electron beam.

In yet another aspect, the high-energy beam may be passed in any desired pattern over a surface with powder particles to be subjected to material bonding.

In a still further aspect of the method of the present invention, an eddy current measuring arrangement with at least one coil arrangement comprising at least one transmitter coil and at least one integrated or separate receiver coil, e.g., a differential or multi-differential coil may be used for the eddy current testing.

In another aspect, in the eddy current testing with the high-energy beam, the coil arrangement may be passed over the surface of a powder layer.

In another aspect of the method, in the eddy current testing, the coil arrangement may surround the high-energy beam.

In another aspect, one or more measured values of the eddy current testing may be used for controlling the layer-by-layer building, for example, the material bonding.

In another aspect, one or more measured values of the eddy current testing may be used for automatic control of parameters of the layer-by-layer building, for example, the material bonding, and/or may be used for determining whether and/or how a finishing is carried out.

In another aspect, measured values of the eddy current testing may be filtered by a high-pass filter on the basis of a different speed of movement of the coil arrangement and the high-energy beam.

The present invention also provides an apparatus for the generative production of a component with a beam generating device and a powder arranging unit. The apparatus is set up in such a way that a high-energy beam of the beam generating device is passed in any desired pattern over a surface with a powder particle layer provided by the powder arranging unit, in order for the surface to undergo material bonding with powder particles in predetermined regions of the powder particle layer. The apparatus further comprises an eddy current measuring arrangement which is capable of carrying out an eddy current testing during the material bonding by the high-energy beam.

In one aspect of the apparatus, the beam generating device may comprise a laser beam or electron beam unit which comprises a deflecting device with which a respective beam can be passed over the surface provided with powder.

In another aspect, the eddy current measuring arrangement may comprise at least one coil arrangement comprising at least one transmitter coil and at least one integrated or separate receiver coil, for example, a differential or multi-differential coil.

In yet another aspect of the apparatus of the present invention, the apparatus may further comprise a control unit which receives measured values of the eddy current measuring arrangement and outputs control data for the beam generating device and/or the powder arranging unit.

The present invention proposes carrying out at the same time as the generative building an eddy current testing, in order to obtain knowledge of the machining process and the layer structure by means of the eddy current testing, so that the homogeneity, and the quality in general, of the layer structure and of the component generated can be improved on the basis of the knowledge acquired about the course of the generative building and/or the properties of the layers deposited.

Correspondingly, in the case of an apparatus for the generative production of components, not only a radiation-generating device for providing a high-energy beam and a powder-arranging unit, by which a layer of powder is provided for the layer-by-layer building of the component to be generated, but also an eddy current measuring arrangement is provided, with which an eddy current testing can be carried out during the material bonding of the powder particles by means of the high-energy beam.

The eddy current measuring arrangement may be equipped with at least one coil arrangement comprising at least one transmitter coil and at least one integrated or separate receiver coil, preferably with a differential or multi-differential coil.

In the case of an integrated receiver coil, the transmitter coil and the receiver coil are realized by one coil, whereas, in the case of separate transmitter and receiver coils, there are separate coils for transmitting and receiving.

In eddy current testing, eddy currents are generated by the transmitter coil in the material to be investigated and in turn generate alternating electromagnetic fields, which can be detected by the receiver coil. By means of the detected electromagnetic fields, conclusions about the material investigated can be drawn and a characterization of the material built up can be carried out.

By means of a differential or multi-differential coil, in which at least two separate receiver coils are provided, external influences on the measurement result, such as for example temperature changes, can be ruled out.

The measured values obtained in the eddy current testing, or at least one corresponding measured value, can be used for the control, and in particular automatic control, of the layer-by-layer building, or in particular the material bonding, in that corresponding parameters of the layer-by-layer building, such as for example the radiation power, setting of the beam diameter, setting of the speed of movement of the beam over the surface to be machined, settings for the exposure strategy, such as for example the exposure sequence, settings for a possible preheating of the powder and/or of the component to be formed, settings for the layer thickness of the powder particles applied and the like, can be varied in dependence on the measurement results.

Correspondingly, the apparatus for the generative production of components according to the present invention may comprise a control unit, which receives the measured values of the eddy current measuring arrangement and outputs control data for the radiation generating device and/or the powder arranging unit. Consequently, the control or operation of the apparatus for the generative production of components can be adapted in situ to the given conditions.

In addition, the results of the eddy current testing can also be used for an optional finishing of the layers applied by the high-energy beam, so that corresponding defects can be repaired or eliminated in finishing with the high-energy beam.

In the layer-by-layer generative production of a component from powder particles, the high-energy beam is usually moved in relation to the surface of the powder particle layer or the component already generated, in order to produce material bonding in the corresponding regions in which the beam impinges on the powder layer. In the simultaneous eddy current testing, the coil arrangement for the eddy current testing with the high-energy beam may be passed over the surface of the powder layer, wherein the speed of movement of the high-energy beam may be greater than the speed of movement of the coil arrangement, since the high-energy beam may be moved additionally in relation to the coil arrangement. On account of this different speed of movement, the measured values of the eddy current measuring arrangement may be subjected to high-pass filtering, in order in this way to improve the signal-to-noise ratio of the measured values.

In particular, the coil arrangement may surround the high-energy beam, so that specifically the machining region of the high-energy beam is subjected to the eddy current testing.

The high-energy beam may be a laser beam or an electron beam or some other suitable beam of an electromagnetic radiation or a corresponding particle beam.

The material bonding between the powder particles or the powder particles and the already existing component may take place by welding or sintering.

BRIEF DESCRIPTION OF THE DRAWINGS

In the purely schematic accompanying drawings.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
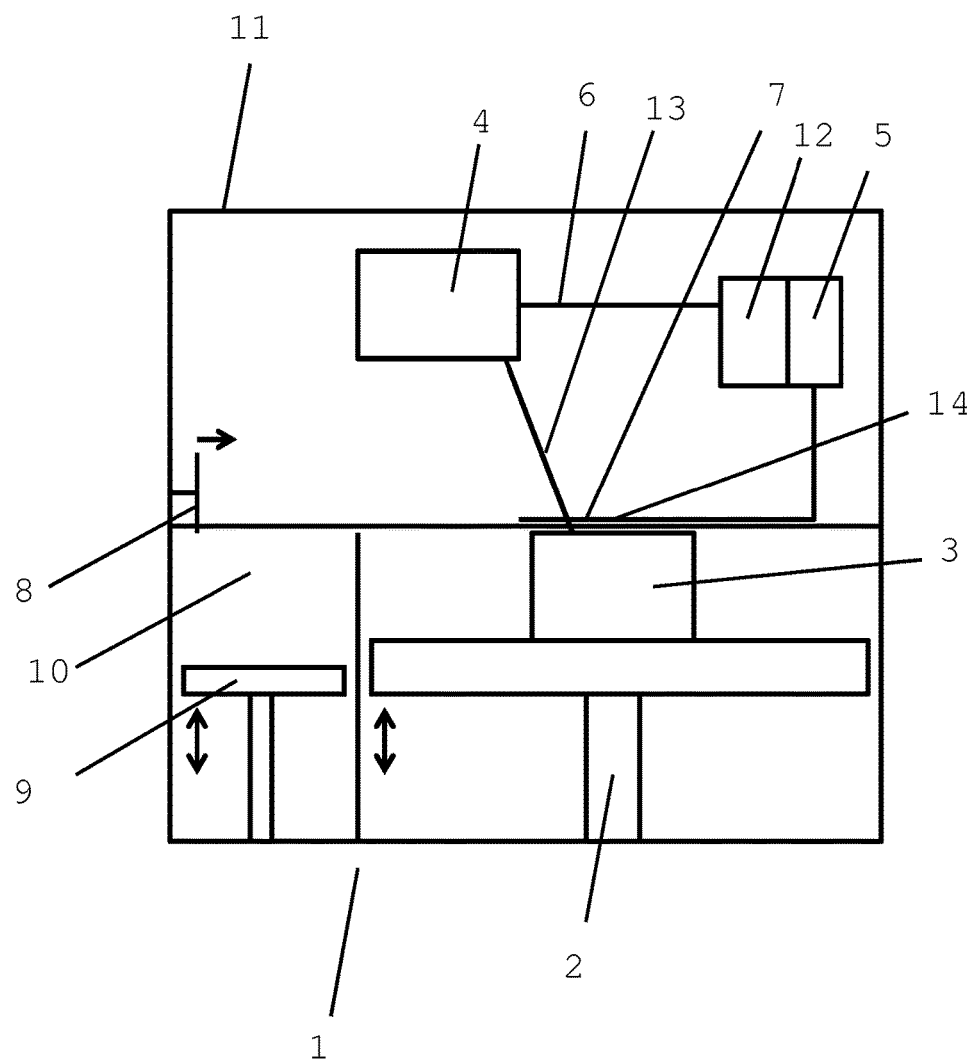
FIG. 1 shows a schematic representation of an apparatus according to the invention for the generative production of components by the example of selective laser melting.

FIG. 1 shows in a purely schematic representation an apparatus 1 according to the invention, as may be used for example for selective laser melting for the generative production of a component. The apparatus 1 comprises a lifting table 2, on the platform of which there is arranged a semifinished product 3, on which material is deposited layer by layer in order to generate a three-dimensional component. For this purpose, powder 10, which is located above a lifting table 9 in a powder store, is pushed by means of the pusher 8 layer by layer over the semifinished product 3 and subsequently bonded with the already present semifinished product 3 by melting or sintering by the laser beam 13 of a laser 4. The bonding of the powder material in a powder layer with the semifinished product 3 takes place by the laser 4 in a way depending on the desired contour of the component to be produced, so that any desired, three-dimensional forms can be generated. In order to avoid undesired reactions with the ambient atmosphere during the melting or sintering, the process may take place in an enclosed space, which is provided by a housing 11 of the apparatus 1, and moreover an inert gas atmosphere may also be provided, in order for example to avoid oxidation of the powder material during the depositing and the like.

The laser beam 13 moves over the powder layer 14 arranged over the component 3, in order to melt the powder material at the locations at which the component 3 is to be generated layer by layer and to enter into a material bond with the already existing component 3. As an alternative to melting, the powder material may also merely be heated up to the extent that a sintering process takes place.

With a deflecting unit that is not represented any more specifically, the laser beam 13 generated by the beam generating unit 4 is deflected in two directions that are independent of one another in such a way that every location of the surface of the powder particle layer 14 can be reached. In this way it is possible to realize any desired three-dimensional form of the component 3 to be produced.

During the interaction of the laser beam 13 with the powder of the powder layer 14, a coil arrangement 7, with which an eddy current testing can be carried out during the melting or sintering of the powder, is provided around the laser beam 13.

The coil arrangement 7 comprises a transmitter coil and at least one receiver coil, preferably two separate receiver coils (not represented), wherein eddy currents are generated by the transmitter coil in the machining region of the laser beam 7 and the magnetic fields induced by the eddy currents are measured by the receiver coil. The measurement of the magnetic fields generated by the eddy currents allows the state of the material in the machining region of the laser beam 13 to be inferred. This knowledge in turn makes it possible to set the settings and parameters of the apparatus for the generative production of the component in dependence on the eddy current testing. For this purpose, the coil arrangement 7 is connected to an actuating unit 5 of the eddy current measuring arrangement, which on the one hand provides the coil current for the coil arrangement 7 and on the other hand receives the measurement data of the coil arrangement 7. Furthermore, the actuating unit 5 brings about the movement of the coil arrangement 7 together with the laser beam 13, wherein the coil arrangement with a single integrated transmitter and receiver coil or separate transmitter and receiver coils can move at a small distance from the machining surface in parallel above the powder layer 14 in two independent directions. The actuating unit 5 of the eddy current measuring arrangement is connected to a control unit 12, which receives the measurement data of the eddy current testing and, in dependence on these measurement data, generates control data for the laser beam generating device 4 and transmits them to the latter via the control data line 6. In addition, the control unit 12 may also supply the lifting tables 2 and 9 and the pusher 8 with control data, in order for example to influence the arrangement of the powder in the powder layer 14 or the thickness of the powder layer 14 or the like in dependence on the eddy current testing. In this way, the control unit 12 can be used to realize automatic control, with which, by means of eddy current testing using the coil arrangement 7, the state of the layer structure on the component 3 is detected and the parameters for the generative production, such as for example beam power, speed of movement of the beam over the surface of the powder layer 14 or the component 3, thickness of the powder layer 14, size of the focal point of the beam, movement sequence of the laser beam 13 (scanning strategy), possible preheating of the powder layer 14 and/or the component 3, for example by inductive heating and the like, are set in situ.

In addition, the knowledge obtained from the eddy current testing may also be used for finishing a layer, that is to say exposing it with the laser beam 13 for a second time, in order to heal defects established in the eddy current testing.

Figure 2:
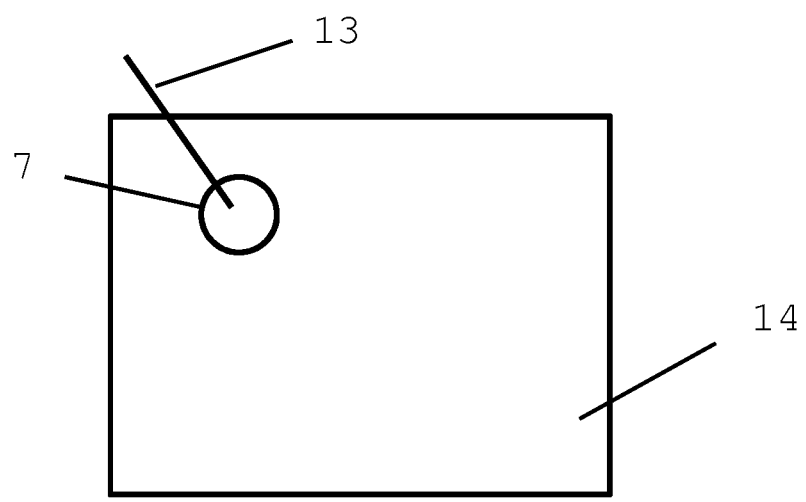
FIG. 2 shows a plan view of a surface of a powder particle layer with a laser beam and a coil arrangement during the application of a layer.

FIG. 2 shows a plan view of the powder layer 14 during machining with the laser beam 13. As can be seen from FIG. 2, provided around the point of impingement of the laser beam 13 on the powder layer 14 or around the laser beam 13 is a coil arrangement 7, which moves with the laser beam 13 over the surface of the powder layer 14. With the aid of the coil arrangement 7, an eddy current testing can be carried out, as described above, in order to be able to adapt the conditions for the generative growth of the layers during the production of the component 3.

The coil of the coil arrangement 7 may have a diameter of up to 5 cm and be moved at a distance of from 0.1 mm to 1 mm from the surface of the powder layer 14 at a speed in the range from 50 mm per second to 2000 mm per second. The laser beam 13 may be additionally moved within the coil arrangement 7 in relation to the coil arrangement 7, for example by a back and forth movement transversely with respect to the forward movement of the laser beam 13 in the machining direction. Correspondingly, the speed of movement of the laser may be higher than the speed of movement of the coil arrangement 7.

Although the present description refers to the movement of the beam and the coil arrangement in relation to the component or semifinished product, it goes without saying that the relative movement may also be realized by a movement of the semifinished product with respect to the beam and the coil arrangement.

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method for generatively producing components by layer-by-layer building from a powder material by selective material bonding of powder particles by a high-energy beam, wherein an eddy current testing is carried out concurrently with the material bonding, an eddy current measuring arrangement with at least one coil arrangement that comprises at least one transmitter coil and at least one integrated or separate receiver coil and surrounds the high-energy beam being used for the eddy current testing.

2. The method of claim 1, wherein the material bonding takes place by at least one of welding and sintering.

3. The method of claim 1, wherein the high-energy beam is a laser beam or an electron beam.

4. The method of claim 1, wherein the high-energy beam is passed in a desired pattern over a surface having thereon powder particles to be subjected to material bonding.

5. The method of claim 1, wherein the coil arrangement comprises a differential or multi-differential coil.

6. The method of claim 1, wherein in the eddy current testing, the coil arrangement is passed over the surface of a powder layer.

7. The method of claim 1, wherein one or more measured values of the eddy current testing are used for automatic control of parameters of the layer-by-layer building.

8. The method of claim 1, wherein one or more measured values of the eddy current testing are used for automatic control of parameters of the material bonding.

9. The method of claim 1, wherein one or more measured values of the eddy current testing are used for determining whether and/or how a finishing is carried out.

10. The method of claim 1, wherein measured values of the eddy current testing are filtered by a high-pass filter on the basis of a different speed of movement of the coil arrangement and the high-energy beam.

11. A method for generatively producing components by layer-by-layer building from a powder material by selective material bonding of powder particles by a high-energy beam, wherein an eddy current testing is carried out concurrently with the material bonding, an eddy current measuring arrangement with at least one coil arrangement which comprises at least one transmitter coil and at least one integrated or separate receiver coil being used for the eddy current testing, and wherein a speed of movement of the high-energy beam is different from a speed of movement of the at least one coil arrangement.

12. The method of claim 11, wherein the speed of movement of the high-energy beam is greater than the speed of movement of the at least one coil arrangement.

13. The method of claim 12, wherein measured values of the eddy current testing are filtered by a high-pass filter on the basis of a different speed of movement of the coil arrangement and the high-energy beam.

14. The method of claim 11, wherein measured values of the eddy current testing are filtered by a high-pass filter on the basis of a different speed of movement of the coil arrangement and the high-energy beam.

15. The method of claim 11, wherein the material bonding takes place by at least one of welding and sintering.

16. The method of claim 11, wherein the high-energy beam is a laser beam or an electron beam.

17. The method of claim 11, wherein the coil arrangement comprises a differential or multi-differential coil.

18. The method of claim 11, wherein one or more measured values of the eddy current testing are used for automatic control of parameters of the layer-by-layer building.

19. The method of claim 11, wherein one or more measured values of the eddy current testing are used for automatic control of parameters of the material bonding.

20. The method of claim 11, wherein one or more measured values of the eddy current testing are used for determining whether and/or how a finishing is carried out.

* * * * *